United States Patent [19]

Patel et al.

[11] Patent Number: 5,164,190
[45] Date of Patent: Nov. 17, 1992

[54] SUBSATURATED TRANSDERMAL DRUG DELIVERY DEVICE EXHIBITING ENHANCED DRUG FLUX

[75] Inventors: Dinesh C. Patel, Murray; Charles D. Ebert, Salt Lake City, both of Utah

[73] Assignee: Theratech, Inc., Salt Lake City, Utah

[21] Appl. No.: 626,685

[22] Filed: Dec. 11, 1990

[51] Int. Cl.$^5$ .............................................. A61F 13/02
[52] U.S. Cl. .................................... 424/448; 424/449
[58] Field of Search ................. 424/448, 449, 447

[56] References Cited

U.S. PATENT DOCUMENTS

| | | |
|---|---|---|
| 4,568,343 | 2/1986 | Leeper et al. .................. 424/449 |
| 4,645,502 | 2/1987 | Gale et al. ...................... 424/449 |
| 4,816,258 | 3/1989 | Nedberge et al. .............. 424/448 |
| 4,849,224 | 7/1989 | Chang et al. ................... 424/434 |
| 4,863,738 | 9/1989 | Taskovich ....................... 424/449 |
| 4,865,848 | 9/1989 | Cheng et al. .................... 424/449 |
| 4,867,982 | 9/1989 | Campbell et al. ............... 424/449 |
| 4,900,555 | 2/1990 | Cheng et al. .................... 424/449 |
| 4,904,475 | 2/1990 | Gale et al. ...................... 424/449 |
| 4,908,027 | 3/1990 | Enscore et al. ................. 424/449 |
| 4,940,586 | 7/1990 | Cheng et al. .................... 424/464 |

*Primary Examiner*—Thurman K. Page
*Assistant Examiner*—Leon R. Horne
*Attorney, Agent, or Firm*—Morrison & Foerster

[57] ABSTRACT

Transdermal administration of hydrophobic drugs via a diffusion mechanism in which the drug is dissolved in a carrier at concentrations that are 20% to 80% of the saturation concentration. The flux of drug from the device is non-Fickian and is substantially greater than the flux observed when the drug is at saturation.

22 Claims, No Drawings

SUBSATURATED TRANSDERMAL DRUG DELIVERY DEVICE EXHIBITING ENHANCED DRUG FLUX

DESCRIPTION

1. Technical Field

This invention is in the field of transdermal drug administration. More particularly it relates to a device and method that provides the drug at unexpectedly high flux.

2. Background

Transdermal drug delivery devices typically comprise a drug reservoir composed of the drug and a carrier from which the drug is released by diffusion. Examples of such devices are described in "Transdermal Drug Delivery Systems," U.S. Pharmacist, pp. 49-78.

Fick's Law has classically been used to characterize the drug release kinetics of such diffusional devices. According to this law the maximum flux of drug from such a device occurs when the concentration of drug in the carrier is at saturation. Correlatively, the art teaches that the maximum flux of the drug across skin (when the skin is not a rate controlling barrier to the drug) from a given drug-carrier combination also occurs when the concentration of drug in the carrier is at saturation. Since maximum skin flux is desired with most drugs, diffusional devices have traditionally been designed to maintain saturation conditions in the carrier over the dispensing lifetime of the device.

Applicants have now unexpectedly discovered that the maximum skin flux from diffusional devices in which the drug is hydrophobic occurs when the drug is maintained below saturation in the carrier. This finding is totally contrary to the conventional wisdom followed in the transdermal drug device art.

Some prior patents have suggested in passing that while it is desirable to maintain the concentration of drug at saturation because maximum flux occurs there at, that the drug concentration could be below saturation. See for instance U.S. Pats. Nos. 4,568,343; 4,645,502; 4,816,258; 4,863,738; 4,865,848; and 4,908,027. These patents, however, fail to suggest maintenance of subsaturation levels of drug throughout the dispensing lifetime or that any increase in skin flux could be achieved with hydrophobic drugs under such conditions.

DISCLOSURE OF THE INVENTION

As described above, the invention is based on the discovery that in the case of transdermal administration of hydrophobic drugs from a diffusional device, maximum skin flux is achieved at concentrations of drug in the carrier that are below saturation. In some instances the increase in flux at subsaturation is dramatically higher than at saturation. The invention thus takes the form of devices for and methods of administering hydrophobic drugs transdermally that are based on this finding.

Accordingly, in one aspect, the invention is a device for administering by diffusion a hydrophobic drug transdermally to a patient for a prolonged time period comprising:

(a) a reservoir comprising the drug dissolved in a carrier, the amount and solubility of the drug in the carrier defining a condition of subsaturation that is sufficient to provide a drug skin flux substantially throughout said time period that is significantly greater than the drug skin flux provided when the carrier is saturated with drug; and (b) means for maintaining the reservoir in drug delivery communication with the skin of the patient.

In another aspect the invention is an improvement in the method for administering a hydrophobic drug transdermally to a patient for a prolonged time period by placing a reservoir comprising the drug dissolved in a carrier in communication with the skin of the patient which improvement comprises having the concentration of the drug in the carrier below saturation at the start of the period and maintaining subsaturation thereafter for a sufficient time to provide substantially throughout the time period a drug skin flux that is substantially greater than the drug skin flux provided when the carrier is saturated with the drug.

Another aspect of the invention is a method of increasing the flux of a hydrophobic drug from a reservoir of the drug dissolved in a carrier that is in drug delivery communication with an area of unbroken skin of a patient for a prolonged time period above the flux provided when the concentration of drug in the carrier is at saturation comprising having the concentration of drug in the carrier at below saturation at the start of the period and maintaining subsaturation thereafter for a time sufficient to provide said increase substantially throughout the time period.

MODES FOR CARRYING OUT THE INVENTION

The term "drug" as used to describe the principal active ingredient of the invention device intends a biologically active compound or mixture of compounds that has a therapeutic, prophylactic and/or physiological effect on the wearer of the device. Examples of the types of drugs that may be used in the device are antiinflammatory drugs, analgesics, antiarthritic drugs, antispasmodics, antidepressants, antipsychotic drugs, tranquilizers, antianxiety drugs, narcotic antagonists, antiparkinsonism agents, cholinergic agonists, anticancer drugs, immunosuppressive agents, antiviral agents, antibiotic agents, appetite suppressants, antiemetics, anticholinergics, antihistamines, antimigrane agents, vasodilators, hormonal agents, contraceptive agents, diuretics, antihypertensive agents, cardiovascular drugs, and the like.

As used herein the term "hydrophobic" intends that the solubility of the drug in water at room temperature is <50 $\mu$g/ml. Specific examples of hydrophobic drugs are steroids such as estrogens, progestogens, testosterone, norgestrel, norethindrone acetate and medroxyprogesterone acetate.

The phrase "prolonged time period" means a period of at least about one day, usually 1-14 days, more usually 1-7 days. The term "substantially throughout" intends at least about 60% of the time period, more usually at least 80%, and preferably 100% of the period.

The term "skin flux" intends the rate of transfer of drug across skin as measured by the method of Merritt and Cooper (*J Controlled Release* (1984) 1:161). The units of flux are preferably $\mu$g/cm$^2$/hr.

The term "significantly greater" that is used to characterize the increase in skin flux achieved through use of the invention will typically denote an increase in skin flux of at least about 25%, usually 25% to 400%, and more usually 50% to 200% over the skin flux provided when the carrier is saturated with the drug.

The devices of the invention release drug continuously by diffusion. In this mode, the driving force is the difference in drug concentration between the device reservoir and the skin and underlying tissue. The drug, which is entirely dissolved in the carrier or vehicle in the case of the present invention, permeates through the carrier to the skin. The carrier is, of course, in drug delivery communication with the skin—which means that it either contacts the skin directly or contacts material interposed between the carrier and the skin that provides a permeation pathway for the drug to migrate from the reservoir to the skin. The interposed material may be homogeneous, heterogeneous, or be composed of a multiplicity of distinct layers. In any event the interposed material is permeable to the drug and preferably is not a rate-controlling barrier to diffusion (i.e., it is at least as permeable to the drug as the carrier).

As indicated above, the carrier or vehicle is permeable to drug. In this regard the diffusion coefficient of the drug in the carrier will usually be between $1 \times 10^{-6}$ and $1 \times 10^{-12}$ cm$^2$/sec, more usually between $1 \times 10^{-7}$ and $1 \times 10^{-10}$ cm$^2$/sec. The solubility of the drug in the carrier should be such that sufficient drug is contained in the device to provide the required cumulative dose of drug, which will vary from drug to drug. At the same time, the solubility should not be so low as to require the device to be impractically large in area or thickness. In most instances, the solubility of drug in the carrier will be in the range of 1 to 500 mg/ml, more usually 1 to 200 mg/ml (measured at room temperature). The amount of drug in the carrier will normally range between 0.001 and 100 mg, more usually between 1 and 50 mg. The thickness of the reservoir will usually be about 0.01 to 5 mm, more usually 0.03 to 2 mm. The area of the device in drug delivery contact with the skin will usually be between about 1 and 150 cm$^2$, more usually between and 5 and 40 cm$^2$.

Preferably, the carrier is a solid or semisolid polymer that enables the device to be a "solidstate" device (i.e., no liquid component at room temperature). Alternatively, the carrier may be in a fluid form (e.g., liquid, gel, emulsion, suspension, and be aqueous or nonaqueous. Examples of fluid carriers that may be used are alcohols such as ethanol, alcohol-water mixtures, and low molecular weight polymers such as polyethylene glycol. Examples of solid polymeric carriers that may be used in this invention are polyacrylates, polymethacrylates, silicone polymers, polyalkyloxides, natural and synthetic rubbers and the dermatologically acceptable adhesives described in U.S. Pat. No. 3,934,097.

The concentration of drug in the carrier will usually be between 20% and 80% of saturation concentration, usually 20% and 60% of saturation substantially throughout the administration period. Depending upon the nature of the carrier and other components of the reservoir (permeation enhancers), the concentration of drug relative to saturation may decrease or increase over the administration period. If the solubility of the drug in the carrier (whether modified or not by other components) remains constant over the period, the concentration relative to saturation will decrease. On the other hand, if the solubility decreases (for instance, through delivery of a permeation enhancer that also increases solubility), then the concentration relative to saturation will increase.

A permeation enhancer may be administered concurrently with the drug in order to further increase the skin flux of drug across the skin. The enhancer may also be contained within the reservoir or be administered from a separate reservoir underlying or overlying the drug reservoir. For design simplicity, when used, the enhancer will preferably be contained in the drug reservoir. Aside from the requirements that the enhancer be compatible with the drug and carrier, there are no limitations on the enhancers that may be used in the invention. Examples of enhancers known in the art are those described in U.S. Pats. Nos. 3,989,816; 4,316,893; 4,863,970; 4,764,379; 4,537,776; and EPA (Pub. No.) 272,987, the disclosures of which, as they relate to enhancers, are incorporated herein by reference.

The device of the invention may be embodied in various types of structures known in the transdermal drug delivery art. For instance, the drug reservoir, which is the most important component of the device, may comprise a simple matrix of a subsaturated solution of the drug in the carrier or be in the form of a fibrous body impregnated with the subsaturated solution of drug in the carrier. In addition to the reservoir, the device includes means for maintaining the reservoir in drug delivery communication with the skin. Such means include a carrier which is also an adhesive, a separate basal adhesive layer underlying the reservoir, a peripheral ring of adhesive that is interconnected to the reservoir, an adhesive overlay for the reservoir, and straps. Preferably the means is either an adhesive carrier or a separate underlying adhesive layer. Preferably the device is in the form of a laminated composite.

In addition to the reservoir and affixation means, the device may further include a backing that overlies the reservoir and protects the reservoir and/or prevents back-diffusion of drug from the reservoir, one or more structural layers to provide the device with appropriate mechanical properties, and/or a release liner layer that underlies the reservoir and which is removed prior to use.

These devices may be manufactured by conventional techniques used in the transdermal drug delivery device art. For instance the drug and carrier may be mixed in the desired proportions to form a homogeneous mix and cast or otherwise applied to a backing layer, followed by lamination to a release liner layer. If a separate basal adhesive layer is desired, it may be cast onto the release liner layer prior to such lamination. As indicated above, the solubility of drug in the carrier and the size (thickness of reservoir and area in drug delivery communication with the skin) are chosen to maintain subsaturation in the reservoir over the desired dispensing lifetime of the device and provide the necessary cumulative dose of drug.

The following examples further illustrate the invention and its unique characteristics. These examples are not intended to limit the invention in any manner. In the following examples in vitro steady state transdermal flux across human cadaver skin was determined using the method of Merritt and Cooper, supra. Unless otherwise indicated percentages and proportions are by volume.

EXAMPLE 1

Formulations of progesterone at varying concentrations were made by mixing progesterone with the indicated ingredients and applied to cadaver skin. The transdermal fluxes for these formulations are reported in Table 1 below. The meanings of the abbreviations that appear in the table are: Gly=glycerine; GDO=- glycerol dioleate; ML=methyl laurate; OA=oleic acid; GMO=glycerol monooleate.

TABLE 1

| Enhancer Systems* | Progesterone Conc. (mg/ml) | N | Flux (μg/cm²/hr) |
|---|---|---|---|
| 1. 60/22.5/10/2.5/2.5/2.5 EtOH/H₂O/Gly/GDO/ML/OA | 75.0 | 8 | 2.12 ± 0.47 |
| 2. 60/22.5/10/2.5/2.5/2.5 EtOH/H₂O/Gly/GDO/ML/OA | 50 | 18 | 4.51 ± 1.37 |
| 3. 60/22.5/10/2.5/2.5/2.5 EtOH/H₂O/Gly/GDO/ML/OA | 25 | 3 | 5.52 ± 1.38 |
| 4. 60/22.5/10/2.5/2.5/2.5 EtOH/H₂O/Gly/GMO/ML/OA | 75 | 8 | 3.35 ± 2.18 |
| 5. 60/22.5/10/2.5/2.5/2.5 EtOH/H₂O/Gly/GMO/ML/OA | 50 | 18 | 7.63 ± 3.00 |
| 6. 60/22.5/10/2.5/2.5/2.5 EtOH/H₂O/Gly/GMO/ML/OA | 37.5 | 6 | 8.18 ± 0.90 |
| 7. 60/22.5/10/2.5/2.5/2.5 EtOH/H₂O/Gly/GMO/ML/OA | 25 | 18 | 6.37 ± 1.88 |
| 8. 60/22.5/10/2.5/2.5/2.5 EtOH/H₂O/Gly/GMO/ML/OA | 10 | 3 | 1.84 ± 0.33 |

*Systems #1–#8 were gelled by adding 2.5% (w/v) Carbopol 1342, pHs were unadjusted (3.2–3.5) and the loading doses were 0.075 ml.

In Table 1, systems 1 and 4 contain progesterone at saturation. Systems 1–3 are alike except for progesterone concentration, and systems 4–8 are alike except for progesterone concentration. The two sets of systems are alike except that one (1–3) contains GDO and the other (4–8) contains GMO. As shown by the flux data in Table 1, the flux is significantly greater in those systems (except 8) in which the progesterone is at subsaturated concentrations (systems 1,3, 5–7) than when the progesterone is at saturation.

EXAMPLE 2

Additional progesterone systems were formulated and tested as in Example 1. The results of these tests are shown in Table 2 below. Abbreviations are as in Example 1. Progesterone was present at saturation in system 1 and below saturation in systems 2–6.

TABLE 2

| Enhancer Systems* | Progesterone Conc. (mg/ml) | N | Flux (μg/cm²/hr) |
|---|---|---|---|
| 1. 60/22.5/10/2.5/2.5/2.5 EtOH/H₂O/Gly/GDO/ML/OA | 50 | 12 | 6.01 ± 1.73 |
| 2. 60/28/10/1/1 EtOH/H₂O/Gly/GMO/ML | 30 | 3 | 13.03 ± 3.35 |
| 3. 60/28/10/1/1 EtOH/H₂O/Gly/GMO/ML | 25 | 3 | 12.98 ± 2.06 |
| 4. 60/28/10/1/1 EtOH/H₂O/Gly/GMO/ML | 20 | 9 | 15.89 ± 6.81 |
| 5. 60/28/10/1/1 EtOH/H₂O/Gly/GMO/ML | 15 | 12 | 13.13 ± 1.87 |
| 6. 60/28/10/1/1/1 EtOH/H₂O/Gly/GMO/ML | 10 | 5 | 11.13 ± 1.98 |

*Systems were gelled by adding 2.5% (w/v) Carbopol 1342 and the loading doses were 0.075 ml.

As in Example 1, the fluxes of progesterone at concentrations below saturation were significantly greater than at saturation.

EXAMPLE 3

This Example shows that the phenomenon of higher drug flux at subsaturation unexpectedly occurs only with hydrophobic drugs.

Formulations of the hydrophilic drugs oxybutynin HCl and mecamylamine HCl were prepared and tested as in Examples 1 and 2. Tables 3 and 4 below report the results of those tests. The formulations of Table 3 containing oxybutynin HCl at 40 mg/ml were saturated and the formulations of Table 4 containing 80 mg/ml of mecamylamine HCl were saturated. All other systems were at drug concentrations below saturation.

TABLE 3

| Enhancer Systems | Oxybutyrin Conc. (mg/ml) | N | Flux (μg/cm²/hr) |
|---|---|---|---|
| 1. 40/53/5/2 EtOH/H₂O/Gly/GMO | 40 | 4 | 29.1 ± 11.2 |
|  | 20 | 12 | 16.9 ± 5.2 |
|  | 10 | 6 | 13.3 ± 2.6 |
|  | 5 | 3 | 5.6 ± 0.9 |
| 2. 40/54/5/1 EtOH/H₂O/Gly/GMO | 40 | 5 | 38.8 ± 18.9 |
|  | 20 | 12 | 17.5 ± 5.1 |
|  | 10 | 6 | 10.1 ± 3.3 |
|  | 5 | 3 | 8.0 ± 1.4 |
| 3. 30/63/5/2 EtOH/H₂O/Gly/GMO | 40 | 6 | 23.9 ± 10.0 |
|  | 20 | 12 | 14.8 ± 6.1 |
|  | 10 | 9 | 8.3 ± 3.8 |
|  | 5 | 3 | 2.2 ± 0.2 |
| 4. 30/64/5/1 EtOH/H₂O/Gly/GMO | 40 | 6 | 27.5 ± 13.1 |
|  | 20 | 15 | 13.6 ± 5.2 |
|  | 10 | 6 | 5.4 ± 2.5 |
|  | 5 | 3 | 1.7 ± 0.3 |

TABLE 4

| Enhancer Systems | Mecamylamine Conc. (mg/ml) | Loading Dose (μl) | N | Flux (μg/cm²/hr) |
|---|---|---|---|---|
| 1. 50/49/1 EtOH/H₂O/GMO | 80 | 400 | 3 | 534.8 ± 56.2 |
|  | 40 | 400 | 3 | 179.1 ± 51.6 |
|  | 20 | 400 | 3 | 126.7 ± 52.8 |
| 2. 50/49/1 EtOH/H₂O/GMO | 80 | 75 | 3 | 96.5 ± 9.2 |
|  | 40 | 75 | 9 | 37.4 ± 11.0 |
|  | 20 | 75 | 3 | 25.1 ± 1.9 |
| 3. 50/44/5/1 EtOH/H₂O/Gly/GMO | 80 | 75 | 6 | 78.4 ± 36.5 |
|  | 40 | 75 | 9 | 26.7 ± 9.5 |

The flux data of Tables 3 and 4 indicate that in each instance the drug release profile was Fickian with flux decreasing with decreasing concentration below saturation.

Similar tests were carried out on ointment and solid matrix systems containing pindolol free base as the hydrophilic drug. Again, systems exhibited classic Fickian dependence of flux on drug concentration.

EXAMPLE 4

Formulations of testosterone at saturation and below saturation were prepared and tested as in Example 1. The carrier used was EtOH/H₂O/Gly/GMO/ML in a ratio of 60/30/5/2.5/2.5. The results of these tests are shown in Table 5 below. The formulations containing 50 mg/ml testosterone were saturated, whereas the systems containing 40 mg/ml and below were subsaturated. The results are expressed in terms of cumulative permeations at 24 hr rather than as flux.

TABLE 5

| | Conc. (mg/ml) | | | | | |
|---|---|---|---|---|---|---|
| | Cumulative Permeation at 24 hr (μg/cm²) | | | | | |
| Skin | 50 | 40 | 30 | 20 | 15 | 5 |
| 1 | 156.04 | 189.44 | 244.37 | 298.68 | — | 340.93 | — |
| 2 | 188.24 | — | — | 407.57 | — | 564.62 | 335.57 |
| 3 | 121.68 | — | — | 317.66 | 550.48 | 386.73 | — |
| 4 | 128.25 | — | — | 429.22 | 386.89 | 281.79 | — |
| 5 | 130.98 | — | — | 232.71 | 212.18 | 262.63 | — |
| Mean | 145.04 | 189.44 | 244.37 | 337.17 | 383.18 | 367.34 | 335.57 |

TABLE 5-continued

| | Conc. (mg/ml) | | | | | |
|---|---|---|---|---|---|---|
| | Cumulative Permeation at 24 hr (µg/cm²) | | | | | |
| Skin | 50 | 40 | 30 | 20 | 15 | 5 |
| SD | 24.55 | — | — | 72.39 | 138.14 | 107.96 | — |

As shown, the permeation was significantly greater when the testosterone present at subsaturation concentrations. Similar tests were carried out using the following carrier compositions:

| EtOH/H₂O/Gly/GMO/ML/OA | 60/27.5/5/2.5/2.5/2.5 |
|---|---|
| EtOH/H₂O/Gly/GMO/ML | 60/33/5/1/1 |
| EtOH/H₂O/Gly/GMO/ML | 60/25/5/5/5 |
| EtOH/H₂O/Gly/GMO/ML | 50/35/5/5/5 |
| EtOH/H₂O/Gly/GMO/ML/OA | 50/37.5/5/2.5/2.5/2.5 |

In each instance the formulations below saturation exhibited higher permeations than the corresponding formulation at saturation.

EXAMPLE 6

Estradiol-containing matrices were prepared by mixing acrylic adhesive (National Starch Durotac 1194), sorbitan monooleate (Arlacel 80) and estradiol at a ratio of 80-X/20/X where X is the proportion (wt %) of estradiol. The cumulative permeation at 24 hr of estradiol from these matrices were tested as above and are reported in Table 7 below. The matrix containing 8% estradiol was saturated; the others were subsaturated.

TABLE 7

| | % Estradiol | | | | | |
|---|---|---|---|---|---|---|
| | 8% | 6% | 4% | 3% | 2% | 1% |
| Cumulative Permeation (µg/cm²) | 12.93 | 22.56 | 44.94 | 40.88 | 28.31 | 11.36 |
| S.D. | 5.25 | 3.03 | 4.46 | 6.64 | 6.24 | 1.40 |

As reported in the table, the maximum permeation values observed at subsaturation were approximately three-fold that observed at saturation.

Similar tests were carried out on estradiol containing matrices in which sorbitan monolaurate was substituted for sorbitan monooleate and in ointments using the carrier EtOH/H₂O/Gly/GMO/ML - 20/60/5/7.5/7.5. In these other estradiol formulations, maximum permeation was observed at estradiol concentrations below saturation.

EXAMPLE 7

Estradiol-containing matrices were prepared and tested as in Example 6 except that these matrices did not contain permeation enhancer (sorbitan monooleate). The cumulative permeations at 24 hr from these matrices are reported in Table 8 below. The matrix containing 8% estradiol was saturated; the others were subsaturated.

TABLE 8

| | % Estradiol | | | | | |
|---|---|---|---|---|---|---|
| | 8% | 6% | 4% | 3% | 2% | 1% |
| Cumulative Permeation (µg/cm²) | 9.20 | 18.42 | 16.11 | 21.21 | 16.55 | 9.33 |
| S.D. | 3.93 | 0.27 | 0.64 | 2.16 | 1.42 | 1.84 |

EXAMPLE 8

Norethindrone acetate-containing matrices were prepared by mixing a cross-linked acrylic adhesive (Monsanto, Gelva 737), permeation enhancer (a 50:50 (w/w) mix of GMO and ML), and norethindrone acetate at a ratio of 80-X/15/X where X is the proportion of norethindrone acetate. Fluxes from these matrices were tested as above and are reported in Table 9 below. The matrix containing 30% norethindrone acetate was saturated; all others were subsaturated.

TABLE 9

| | % Norethindrone Acetate | | | | |
|---|---|---|---|---|---|
| | 5% | 8% | 10% | 15% | 30% |
| Flux (µg/cm²/hr) | 0.44 | 0.65 | 0.93 | 0.46 | 0.35 |

As reported, the fluxes from the subsaturated matrices were significantly higher than the flux from the matrix that contained the drug at saturation.

Modifications of the above-described modes for carrying out the invention that are obvious to those of skill in the art of transdermal drug delivery and the specific fields encompassed thereby are intended to be within the scope of the following claims.

We claim:

1. A device for administering by diffusion a hydrophobic drug transdermally to a patient for a prolonged time period of at least about one day comprising:
   (a) a reservoir comprising the drug dissolved in a carrier, the amount and solubiilty of the drug in the carrier defining a condition of subsaturation that is sufficient to provide a drug skin flux over at least about 60% of said time period that is at least about 25% greater than the drug skin flux provided when the carrier is saturated with drug; and
   (b) means for maintaining the reservoir in drug delivery communication with the skin of the patient.

2. The device of claim 1 wherein the reservoir also contains a permeation enhancer.

3. The device of claim 1 wherein the hydrophobic drug has a solubility in water at room temperature <50 µg/ml.

4. The device of claim 1 wherein the hydrophobic drug is estradiol, progesterone, testosterone, norethindrone acetate, or medroxyprogesterone acetate.

5. The device of claim 1 wherein the prolonged time period is 1 to 14 days.

6. The device of claim 1 wherein the carrier is a solid and is a polyacrylate, polymethacrylate, silicone polymer, polyalkyloxide, natural rubber or synthetic rubber.

7. The device of claim 1 wherein the carrier is a fluid and is an alcohol, an alcohol-water mixture, or a low molecular weight polymer.

8. The device of claim 1 wherein the solubility of the drug in the carrier is in the range of 1 to 500 mg/ml.

9. The device of claim 1 wherein the drug skin flux over at least about 60% of the time period is 25% to 400% greater than the drug skin flux provided when the carrier is saturated with drug.

10. The device of claim 1 wherein the concentration of drug in the carrier is about 20% to about 80% the saturation concentration of drug in the carrier over at least about 60% of the time period.

11. The device of claim 1 wherein said means is the carrier and the carrier is an adhesive.

12. The device of claim 1 wherein said means is a basal adhesive layer underlying the reservoir, an adhesive overlay, or a ring of adhesive that is peripheral to the reservoir and is interconnected to the reservoir.

13. In a method of administering by diffusion a hydrophobic drug transdermally to a patient for a prolonged time period of at least about one day by placing a reservoir comprising the drug dissolved in a carrier in communication with the skin of the patient the improvement comprising having the concentration of drug in the carrier at below saturation at the start of the period and maintaining subsaturation thereafter for at least about 60% the time period whereby the flux of the drug through the skin over at least about 60% of the time period is at least about 25% greater than the flux of drug provided when the carrier is saturated with drug.

14. The method of claim 13 wherein the hydrophobic drug is estradiol, progesterone, testosterone, norethindrone acetate, or medroxy progesterone acetate.

15. The method of claim 13 wherein the carrier is a solid and is polyacrylate, polymethacrylate, silicone polymer, polyalkyloxide, natural rubber or synthetic rubber.

16. The method of claim 13 wherein the carrier is a fluid and is an alcohol, an alcohol-water mixture, or a low molecular weight polymer.

17. The method of claim 13 wherein the concentration of drug in the carrier is maintained at 20% to 80% of saturation concentration over at least about 60% of the time period.

18. A method of increasing the flux of a hydrophobic drug from a reservoir of the drug dissolved in a carrier that is in drug delivery communication with an area of unbroken skin of a patient for a prolonged time period of at least about one day above the flux provided when the concentration of drug in the carrier is at saturation comprising having the concentration of drug in the carrier at below saturation at the start of the period and maintaining subsaturation thereafter for at least about 60% of the time period to provide an increase in the flux of at least about 25% greater than the flux of drug provided when the carrier is saturated with drug over at least about 60% of the time period.

19. The method of claim 18 wherein the hydrophobic drug is estradiol, progesterone, testosterone, norethindrone acetate, or medroxyprogesterone acetate.

20. The method of claim 18 wherein the carrier is a polyacrylate, polymethacrylate, silicone polymer, polyalkyloxide, natural rubber or synthetic rubber.

21. The method of claim 18 wherein the carrier is a fluid and is an alcohol, an alcohol-water mixture, or a low molecular weight polymer.

22. The method of claim 18 wherein the concentration of drug in the carrier is maintained at 20% to 80% of saturation concentration over at least about 60% of the time period.

* * * * *